United States Patent [19]

Williams et al.

[11] Patent Number: 4,883,657

[45] Date of Patent: Nov. 28, 1989

[54] REARRANGER PROCESS AND COMPOSITION FOR PERMANENT WAVING PROCESS

[75] Inventors: Barry W. Williams, Chicago, Ill.; Pamela M. Daniels, Gary, Ind.

[73] Assignee: Soft Sheen Products, Inc., Chicago, Ill.

[21] Appl. No.: 158,209

[22] Filed: Feb. 19, 1988

[51] Int. Cl.$^4$ .......................... A61K 7/09; A45D 7/04
[52] U.S. Cl. ...................................... 424/72; 132/204; 132/205
[58] Field of Search .................... 424/72; 132/204, 205

[56] References Cited

U.S. PATENT DOCUMENTS

| | | | |
|---|---|---|---|
| 4,391,286 | 7/1983 | Hsiung et al. | 132/204 |
| 4,416,297 | 11/1983 | Wolfram et al. | 424/71 X |
| 4,572,220 | 2/1986 | Hsiung et al. | 132/203 |
| 4,588,760 | 5/1986 | Jachowicz et al. | 524/12 |
| 4,602,648 | 7/1986 | Syed et al. | 132/204 |

OTHER PUBLICATIONS

"Guar Gum and Its Application", by R. J. Chudzikowski, Soc. Cosmet. Chem. 22, 43–60 (1971), Society of Cosmetic Chemist of Great Britian.

Celanese Corporation Product Bulletins Nos. 114, 38, 23, 122, CN 175, CN 176, CN 174, 117, 118, 123, 124, 180.

A Product Brochure from High-Tek Polymers Inc.

*Primary Examiner*—Thurman K. Page
*Assistant Examiner*—Susan S. Rucker
*Attorney, Agent, or Firm*—Allegretti & Witcoff, Ltd.

[57] ABSTRACT

An improved rearranging composition and permanent waving process is disclosed. The improved waving process produces hair that is characterized as thicker, more full bodied with improved humectant properties and requiring significantly less maintenance than is typically required when conventional waving processes are used. The waving process is a step by step procedure involving the addition of a rearranger, a wrapping lotion, and a neutralizer, in combination with intermittent rinsing. The improved quality and settability of the hair is believed to be attributable to the improved rearranging composition. The rearranging composition comprises a homogeneous mixture of a salt of thioglycolic acid and a homopolymer of methylacrylamidopropyl-trimethyl ammonium chloride (MAPTAC). A preferred rearranging composition includes a weight ratio of ammonium thioglycolate to monoethanolamine thioglycolate of from about 4:6 to about 7:3 and between about 1.0 to about 3.0% by weight of a cationic homopolymer of MAPTAC. The rearranging composition should also be pH adjusted to between about 3.0 to about 10.5.

13 Claims, No Drawings

REARRANGER PROCESS AND COMPOSITION FOR PERMANENT WAVING PROCESS

BACKGROUND OF THE INVENTION

1. Field of Invention

This invention relates broadly to a hair waving or curling process and a novel rearranging waving lotion composition for use in a waving or curling process.

2. Prior Art

Among the components of hair is a proteinaceous material called "keratin". The hair's keratin is made up of long fibrous polypeptide chains which are bonded together with horizontal cross bonds of two forms: Hydrogen bonds and cystine bonds, also sometimes referred to as disulfide bonds.

Cystine bonds play an essential role in determining the degree of curl in hair. Some researchers in the field believe that straight or slightly wavy hair has relatively fewer cystine bonds and relies heavily upon hydrogen bonding to produce curl or waves in the hair and that very curly hair has a relatively larger amount of cystine bonds. Other researchers in the field believe that straight hair and curly hair may have the same number of cystine bonds, but that the cystine bonds present in straight hair tend to occur in a relatively straight alignment, whereas the cystine bonds present in curly hair tend to occur out of alignment. Regardless of which theory is accepted, while the hydrogen bonds can be broken merely by wetting the hair, such that straight or slightly wavy hair will lose virtually all body when wet, very curly hair maintains its body even when wet because the cystine bonds are relatively unaffected by water. Thus, very curly hair cannot be easily reset into new or different hair styles different from its natural state merely by wetting and shaping the hair.

Permanent hair waving is usually carried out by subjecting the hair to a strong reducing agent, such as hydroxide or, more commonly, materials containing a free "-SH" group or thiol. These "thiol" materials are also called mercaptans. In this treatment, the hair is saturated with the thiol agent, which then acts to break the disulfide bonds.

When a sufficient number of hair disulfide bonds habe been broken, the hair is rinsed, removing the unreacted thiol waving agent and disulfide reaction product. The hair is then realigned, e.g., usually by winding on rollers, in order to physically align previously unpaired hair protein bonds, i.e., one-half of the cystine groups. The hair and rollers are then saturated with an oxidizing agent, or neutralizer, such as hydrogen peroxide or a bromate salt, to reform disulfide bonds between the newly paired hair protein thiols and to give the hair a configuration of wave. This general process may be used to either add curl or straighten the hair.

Salts of thioglycolic acid, such as ammonium thioglycolate, and thioglycolic acid esters, such as glycerol thioglycolate, are typically utilized as the thiol waving agent. Other thiol-containing reagents such as thiolactic acid, betamercaptopropionic acid, beta-mercaptobutyric acid, mercaptosuccinic acid and alike have been suggested in the art to be effective.

Prior art waving processes are plagued with the problem of either underwaving or overwaving (under or over processing) that occurs during waving on different parts of a single hair fiber or different areas of the hair mass due to the physical or chemical condition of the hair itself. For example, hair which has been waved, or bleached, or both is more porous than hair which has not undergone these chemical treatments, e.g., portions of the hair fiber near the hair root which has grown out since the last bleaching or waving. Similarly, even hair having no previous history of bleaching or waving is more porous near the tip end than near the root end simply because hair near the tip has been brushed more, or has been subjected to more weathering.

As a consequence of these porosity differences, the hair tends to take up more waving agent in some areas and less waving agent in others. Over waving or processing tends to occur in the more porous portions of the hair while underwaving or processing tends to occur in less porous areas. These trends are exactly the inverse of what is desired since the hair which usually need the waving treatment the most gets the least waving, and visa versa.

Many products today are directed to the special problems and needs of the Black ethnic market. People in the Black ethnic market have, for example, hair characterized by a relatively large number of cystine bonds and relatively high dryness. Conventional permanent waving products have particular limitations applied to this market. Typically, the products result in a hair style that is either very curly and quite greasy or relatively straight and stiff and very dry. These prior products are characterized by the need for frequent, heavy maintenance, e.g., the consumer's application of activators and moisturizers on a daily basis or more than daily basis. None of the prior art compounds are able to produce a Black ethnic hairstyle characterized by thick, full-bodied hair fibers which form loose bouncy curls having good moisture retention.

One of the problems associated with prior art permanent waving process is that they dry the hair to a substantial degree. This problem becomes particularly significant for hair that is relatively dry to begin with. As a result, the prior art processes are associated with with need for frequent and repeated use of moisturizers to maintain the hair. This problem is both inconvenient and expensive for the consumer. It also imposes limitations on the type of hair style that may be achieved with prior waving processes.

Another problem that occurs during the hair disulfide bond breaking process is skin irritation caused by the thiol-containing agents. Irritation occurs usually because beauticians frequently use their bare fingers for the wrapping process.

All of the known waving processes and solutions associated therewith are limited in their ability to produce a looser, bouncier, curl while maintaining the moisture of the curls. The present invention provides an improved in hair waving process, eliminating many of the problems associated with prior art processes and solutions.

SUMMARY OF THE INVENTION

Thus, an object of the present invention is to provide an improved hair waving process and further to provide an improved rearranger composition for use in a hair waving process.

It is an object of this invention to provide a permanent waving process and rearranger that produces hair with improved humectant qualities and that requires less maintenance.

Accordingly, in a broad embodiment, the present invention is a process of waving hair by applying to the hair a particular rearranging composition with chemical properties sufficient to change the alignment of the cystine bonds in the hair keratin. After the rearranger has been left on the hair for a time to accomplish conversion of the bonds, the hair is rinsed to flush away a substantial portion of the rearranging composition. The rearranging composition comprises a homogenous mixture of a salt of thioglycolic acid and a cationic homopolymer of methylacrylamidopropyltrimethyl ammonium chloride. A wrapping lotion composition is then applied to the hair. The hair, with wrapping lotion applied, is wrapped around a rod or roller to produce a desired curl pattern. The hair with wrapping lotion applied is left on the rods for a predetermined length of time, preferably about 5 to about 15 minutes, in order to set or lock in the desired curl pattern. The wrapped hair is rinsed to flush away excess wrapping lotion composition.

After rinsing, a neutralizer composition is applied to the hair, still on the rods, to lock in the curl pattern. The neutralizer is left on the hair for a sufficient period of time to reestablish the cystine bonds, after which the neutralizer is flushed away by rinsing the hair.

The improved rearranger comprises a salt of thioglycolatic acid and between about 1.00 and about 3.0% by weight of a cationic homopolymer of methacrylamidopropyltrimethyl ammonium chloride. In preferred form the rearranger also includes between about 6.0 and about 10.0% by weight of ammonium thioglycolate, between about 3.0 and about 7.0% by weight of monoethanolamine thioglycolate. Also, in preferred form, the rearranger has a pH of between about 8.0 and about 10.5.

These as well as other objects and embodiments will become apparent upon review of the more detailed description of the invention hereinafter set forth.

DETAILED DESCRIPTION OF THE INVENTION

The waving process of the instant invention is comprised of several steps, some of which involve the application of specific hair treatment formulations. As a first step, a rearranging composition is applied to the hair to perform a straightening function. The rearranging composition contains an aqueous solution of chemical agents capable of reducing the disulfide linkages in hair keratin. Suitable chemical agents include water soluable mercaptans, e.g. salts of thioglycolic acid, such as sodium, monoethanolamine, or ammonium thioglycolate, and magnesium thioglycolate. Other soluble mercaptans include thioglycerol, sodium or potassium borohydride, and sodium or ammonium sulfite. The amount of these chemical agents may vary depending on, among other things, the degree of straightening desired, hair treatment history, and the chemical nature of the particular hair to be treated.

A preferred rearranging composition comprises a mixture of ammonium thioglycolate and monoethanolamine thioglycolate ("MEA-Thio"). However, it is within the scope of the invention that either thioglycolate compound may be used alone or as a substitute for the other. When a mixture of the two is used, the ammonium thioglycolate is preferably present inconcentration ranges of about 6.0 to about 10.0% by weight of the rearranging composition, and the MEA-Thio is preferably present in concentrations of about 3.0 to about 7.0% by weight of the total composition. The ammonium thioglycolate and MEA-Thio together preferably comprise between about 7.0% and about 16.0% by weight of the total rearranger composition. A most preferred rearranging composition comprises about 8.0% by weight of ammonium thioglycolate and about 5.5% by weight MEA-Thio. Alternatively, the rearranging composition may be characterized by the weight ratio of ammonium thioglycolate to MEA-Thio. A preferred ratio is between about 4:6 about 7:3 ammonium thioglycolate to MEA-Thio, with a most preferred ratio of 6:4. When only one salt of thioglycolic acid is used, the preferred concentration is between about 5.0 and about 20% by weight. Additionally, a variety of conventional additives may be present in the rearranging composition, such as, conditioners perfumes, emollients, etc. The pH of the composition is adjusted to between 8.0 and 10.5, preferably using ammonium hydroxide. Surprisingly and unexpectedly it has been found that the addition of a polyquaternary amine salt to the rearranging composition has a significant affect on the quality and settability of the hair both during and long after the waving process. The preferred polyquaternary amine salt is a highly charge cationic homopolymer of methacrylamidopropyltrimethyl ammonium chloride (MAPTAC). A preferred concentration of MAPTAC is from between about 1.0 to about 3.0% by weight of the rearranging composition, with a most preferred concentration of about 2.0% by weight. The average molecular weight of the MAPTAC homopolymer ranges from about 100,000 to about 200,000.

Although not completely understood it is believed that the MAPTAC increases the longevity of the curl pattern and the humectant qualities of the hair by penetrating the hair. When the neutralizer solution is applied the polymer is believed to become "locked" into the hair. The increased integrity of the hair and the curl pattern that results from the application of MAPTAC greatly reduces the need for maintenance between subsequent waving treatments.

Additionally, a variety of conventional additives may be present in the rearranging composition, such as, conditioners, perfumes, moisturizers, emollients, etc. The pH of the composition is adjusted to between 8.0 and 10.5 using, preferably, ammonium hydroxide.

The rearranging composition is initially applied to the head and worked into the hair with gentle combing. The rearranging composition is allowed to stand, on the hair for about 5-15 or 20 minutes while the cystine bonds are being broken, the length of time the rearranger is allowed to stand depends upon the degree of curl in the hair's natural state and the degree of straightness desired.

After the hair has straightened to the desired degree, the hair is rinsed, preferably with warm water for about 3-5 minutes to flush away the major portion, preferably all, of the rearranging composition. In this way, the rearranging composition and the wrapping lotion composition are not applied to the hair at the same time.

After the hair has been rinsed, a wrapping lotion or booster is applied to the head and gently massaged into the hair. The hair is then wrapped on rods, curlers, rollers or any other means known to the art to produce or establish a desired curl pattern. The wrapped hair containing the wrapping lotion is allowed to stand for a period of about 5-15 minutes, while the pattern of the curl becomes set. The advantages of the rearranger disclosed herein are believed to occur even if the rearranger is used with any conventional wave wrapping lotion or booster.

After the wrapping lotion has been allowed to stand on the wrapped hair for a period of about 5 to about 15 minutes, the wrapped hair is then rinsed with warm water to remove any excess of wrapping lotion composition.

After rinsing, a neutralizer is applied to the wrapped hair to restore the disulfide linkages in the hair keratin. The neutralizer "locks in" the curl pattern that was formed in the previous steps of the waving process. The exact composition of the neutralizer is not believed critical to achieve the improved results obtained by the waving process of the invention. As known to the art, neutralizers are typically aqueous solutions containing oxidizing agents, such as, sodium bromate. Other ingredients may be added to the neutralizer composition to improve the aesthetic properties of the hair. In particular, it has been found that the addition of from about 1.0 to about 5.0% by weight of ethoxylated castor oil greatly improves the sheen quality of the hair.

After application of the neutralizer, the wrapped hair is then rinsed with warm water to remove a substantial portion, preferably all, of the neutralizer composition. The rods are then removed and the hair is again rinsed with water. As an optional post-treatment step a sealer may be applied to the hair to alleviate the initial dryness that sometimes results immediately after the hair has undergone a waving process. Well known to the art, sealers contain conditioners and humectants.

In order to more fully demonstrate the attendant advantages arising from the present invention, the following examples are set forth. It is to be understood that the following is by way of example of only and is not intended as an undue limitation on the otherwise broad scope of invention.

EXAMPLE I

In accordance with the invention a rearranging composition was prepared for use and evaluation in a waving process. A first solution was prepared by combining and mixing deionized water and a cationic homopolymer of MAPTAC. This solution was then heated to about 80° C. A second soultion of surfactants, conditioners and moisturizers was prepared and heated to about 80° C. The second solution was combined with the first solution and mixed for about 20 minutes and the resultant admixture was allowed to cool to about 50° C. A third solution of monoethanolamine thioglycolate, fragrance and a pH adjuster was then added to the admixture and mixed slowly until a homogenous solution was obtained. The relative weight fractions of the components in the composition, designated as formulation A, are listed in Table II.

TABLE I

|  | Formulation A | Formulation B |
|---|---|---|
| Deionized H$_2$O | 59.7 | 59.6 |
| MAPTAC | 2.0 | — |
| Ammonium Thioglycolate | 8.0 | 10.0 |
| MEA Thioglycolate | 5.5 | — |
| Other Ingredients[1] | 24.8 | 30.4 |

[1]Conditioners, surfactants, pH adjusters, moisturizers and fragrance.

EXAMPLE II

For comparison to the rearranging composition of the invention a conventional prior art rearranger was prepared. The procedure used to make the prior art rearranger was exactly the same as that used to prepare the rearranger of the invention described in Example I, with the exception of the homopolymer of MAPTAC. Additionally, only ammonium thioglycolate was used as the active salt of thioglycolic acid. The absence of MEA thioglycolate did not affect the validity of the comparison. Table I contains the relative weight fractions of the prior art rearranger, designated as formulation B.

EXAMPLE III

A waving process in accordance with the invention was performed using the rearranging composition of Example I. The first step in the process involved pre-shampooing the head with a suitable conditioning shampoo. The hair was then towel blotted dry. The rearranging composition of Example I was then applied to the hair by a tint-brush procedure in an effect to minimize scalp irritation. The rearranger used comprised a homogenous mixture of MEA thioglycolate and a homopolymer of MAPTAC. The rearranger was allowed to stand on the hair for about 10 to 15 minutes until straight.

After the processing with the rearranger was completed the hair was rinsed thoroughly for about 3 to 5 minutes with warm water, then towel blotted dry. A wrapping lotion was then applied in ¼ head sections. The hair in each ¼ section was then wrapped on rods to produce a curl pattern. After roding, the wrapping lotion was allowed to stand on the hair for about 10 minutes.

The hair with the rods intact was then rinsed thoroughly with warm water and then towel blotted dry.

A conventional neutralizer solution having sodium bromate as the active ingredient was then applied sparingly to each rodded portion of hair and allowed to stand for about 10 minutes under a plastic wrap. After processing with the neutralizer, the rodded hair was then rinsed well with warm water for about 3 to 5 minutes to substantially remove the neutralizer. The hair was then unrodded, rinsed again, and dried under a conventional hair dryer.

The resultant hair style obtained from the waving process of the instant invention was characterized as being thicker, more full bodied than hair styles previously possible using prior art waving process. In addition, the longevity of the curl pattern produced and humectant qualities of the hair was increased on a relatively long term bases with substantially lower need for application of maintenance products. The improved hair characteristics obtained as a result of the instant process is believe directly attributable to the use of the improved rearranging composition containing the homopolymer of MAPTAC.

EXAMPLE IV

For the purposes of comparison to the improved waving process of the invention as described in Example III, a conventional prior art waving process was performed. The procedure used for the conventional waving process was identical to that of the waving process of Example III with the exception that the rearranger used did not contain a homopolymer of MAPTAC. The rearranger used was the formulation described above in Example II.

The resultant hair style obtained from the conventional waving process was characterized as relatively tightly curled, dry, and frizzy in appearance. Furthermore, this style required the application of maintenance products, such as, moisturizers and curl activators. These maintenance caused an overall greasy look of the hair style.

The foregoing examples and specification disclose preferred and generalized illustrations if the invention. However, variations are possible within the scope of the invention. For example, the rearranger of this invention is believed to provide advantages when used with any wave wrapping lotion, booster or neutralizer. It should be understood, therefore, that the invention is to be limited only by the following claims and their equivalents.

What is claimed:

1. A process for waving hair, comprising the following steps in combination:
    (a) applying to the hair a rearranging composition with chemical properties sufficient to break the cystine bonds in the hair keratin, said rearranging composition comprises a homogenous mixture of a salt of thioglycolic acid, and a cationic homopolymer of methylacrylamidopropyltrimethyl ammonium chloride;
    (b) rinsing the hair to substantially remove the rearranging composition;
    (c) applying a wrapping lotion composition to the hair;
    (d) wrapping the hair around a rod to produce a curl pattern and allowing the hair and wrapping lotion to set for a predetermined length of time;
    (e) rinsing the wrapped hair;
    (f) applying a neutralizer composition to the curl pattern; and
    (g) rinsing the hair to substantially remove the neutralizer composition, whereby the process produces thicker, fuller hair with loose, bouncy curls.

2. The process of claim 1 wherein the rearranging composition comprises:
    (a) between about 5.0 and about 20% by weight of a salt of thioglycolic acid; and
    (b) between about 1.0 and about 3.0% by weight of a cationic homopolymer of methylacrylamidopropyltrimethyl ammonium chloride.

3. The process of claim 2 wherein the salt of thioglycolic acid comprises ammonium thioglycolate.

4. The process of claim 2 wherein the salt of thioglycolic acid comprises monoethanolamine thioglycolate.

5. The process of claim 2 wherein the salt of thioglycolic acid comprises ammonium thioglycolate and monoethanolamine thioglycolate.

6. The process of claim 5 wherein the weight ratio of ammonium thioglycolate to monoethanolamine is between about 4:6 and about 7:3.

7. The process of claim 1 wherein the rearranging composition is at a pH of between about 8.0 and about 10.5.

8. The rearranging compositions of improving the quality and settability of hair comprising, in combination:
    (a) between about 5.0 and about 20% by weight of a salt of thioglycolic acid; and
    (b) between about 1.0 and about 3.0% be weight of a cationic homopolymer of methylacrylamidopropyltrimethyl ammonium chloride.

9. The composition of claim 8 wherein the salt of thioglycolic acid comprises ammonium thioglycolate.

10. The composition of claim 8 wherein the salt of thioglycolic acid comprises monoethanolamine thioglycolate.

11. The composition of claim 8 wherein the salt of thioglycolic acid comprises ammonium thioglycolate and monoethanolamine thioglycolate.

12. The composition of claim 11 wherein the weight ratio of ammonium thioglycolate to monoethanolamine is between about 4:6 and about 7:3.

13. The composition of claim 8 wherein the rearranging composition is at a pH of between about 8.0 and about 10.5.

* * * * *

REEXAMINATION CERTIFICATE (1702nd)

United States Patent [19]

Williams et al.

[11] B1 4,883,657

[45] Certificate Issued May 12, 1992

[54] REARRANGER PROCESS AND COMPOSITION FOR PERMANENT WAVING PROCESS

[75] Inventors: Barry W. Williams, Chicago, Ill.; Pamela M. Daniels, Gary, Ind.

[73] Assignee: Amethyst Investment Group, Inc.

Reexamination Request:
No. 90/002,208, Nov. 20, 1990

Reexamination Certificate for:
Patent No.: 4,883,657
Issued: Nov. 28, 1989
Appl. No.: 158,209
Filed: Feb. 19, 1988

[51] Int. Cl.$^5$ .................. A61K 7/09; A61K 7/11
[52] U.S. Cl. .................. 424/72; 132/204; 132/205
[58] Field of Search .......... 424/72, 81; 132/204, 132/205, 209

[56] References Cited

U.S. PATENT DOCUMENTS

| | | | |
|---|---|---|---|
| 4,391,286 | 7/1983 | Hsiung et al. | 424/72 X |
| 4,816,246 | 3/1989 | Mathews et al. | 424/72 |
| 4,883,657 | 11/1989 | Williams et al. | 424/72 |

FOREIGN PATENT DOCUMENTS 2114616B 12/1985 United Kingdom .

*Primary Examiner*—Thurman K. Page

[57] ABSTRACT

An improved rearranging composition and permanent waving process is disclosed. The improved waving process produces hair that is characterized as thicker, more full bodied with improved humectant properties and requiring significantly less maintenance than is typically required when conventional waving processes are used. The waving process is a step by step procedure involving the addition of a rearranger, a wrapping lotion, and a neutralizer, in combination with intermittent rinsing. The improved quality and settability of the hair is believed to be attributable to the improved rearranging composition. The rearranging composition comprises a homogeneous mixture of a salt of thioglycolic acid and a homopolymer of methylacrylamidopropyltrimethyl ammonium chloride (MAPTAC). A preferred rearranging composition includes a weight ratio of ammonium thioglycolate to monoethanolamine thioglycolate of from about 4:6 to about 7:3 and between about 1.0 to about 3.0% by weight of a cationic homopolymer of MAPTAC. The rearranging composition should also be pH adjusted to between about 3.0 to about 10.5.

REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1-13 are cancelled.

* * * * *